United States Patent
Kovacevic

(10) Patent No.: US 7,381,223 B2
(45) Date of Patent: Jun. 3, 2008

(54) DUAL-TRAY PROSTHESIS

(76) Inventor: Nebojsa Kovacevic, 1304 W. Medicine Lake Dr., Plymouth, MN (US) 55441

( * ) Notice: Subject to any disclaimer, the term of this patent is extended or adjusted under 35 U.S.C. 154(b) by 0 days.

(21) Appl. No.: 11/302,021

(22) Filed: Dec. 13, 2005

(65) Prior Publication Data

US 2006/0095135 A1   May 4, 2006

Related U.S. Application Data

(63) Continuation of application No. 11/002,340, filed on Dec. 2, 2004, now Pat. No. 7,179,295, and a continuation-in-part of application No. 10/431,207, filed on May 7, 2003, now abandoned, and a continuation-in-part of application No. 10/431,206, filed on May 7, 2003, now abandoned, and a continuation-in-part of application No. 09/972,074, filed on Oct. 5, 2001, now abandoned.

(60) Provisional application No. 60/526,726, filed on Dec. 3, 2003.

(51) Int. Cl.
  *A61F 2/38* (2006.01)
(52) U.S. Cl. .................. 623/20.32; 623/17.15
(58) Field of Classification Search ............ 623/17.15, 623/20.32, 20.33, 20.28, 20.29
  See application file for complete search history.

(56) References Cited

U.S. PATENT DOCUMENTS

| | | | |
|---|---|---|---|
| 1,676,799 A * | 7/1928 | Prouty et al. ............... | 432/258 |
| 1,965,305 A * | 7/1934 | Carlson ..................... | 273/150 |
| 2,985,924 A * | 5/1961 | Burke ........................ | 52/8 |
| 3,115,253 A * | 12/1963 | Malbin et al. ........... | 211/128.1 |
| 4,309,777 A * | 1/1982 | Patil ......................... | 623/17.13 |
| 4,711,639 A * | 12/1987 | Grundei .................... | 623/20.33 |
| 4,832,540 A * | 5/1989 | Kiger et al. ................ | 407/34 |
| 4,883,488 A * | 11/1989 | Bloebaum et al. ....... | 623/20.34 |
| 5,002,576 A * | 3/1991 | Fuhrmann et al. ....... | 623/17.15 |
| 5,062,850 A * | 11/1991 | MacMillan et al. ...... | 623/17.11 |
| 5,080,674 A * | 1/1992 | Jacobs et al. ............ | 623/20.17 |
| 5,197,488 A | 3/1993 | Kovacevic ................. | 128/782 |
| 5,197,987 A * | 3/1993 | Koch et al. ............... | 623/20.28 |
| 5,292,481 A * | 3/1994 | Aspden et al. ............ | 422/53 |
| 5,312,216 A * | 5/1994 | Hogg ........................ | 623/22.4 |
| 5,320,644 A * | 6/1994 | Baumgartner ............ | 623/17.16 |
| 5,358,530 A * | 10/1994 | Hodorek .................. | 623/20.29 |
| 5,360,016 A | 11/1994 | Kovacevic ................. | 128/782 |
| 5,458,642 A * | 10/1995 | Beer et al. ............... | 623/17.13 |
| 5,827,328 A * | 10/1998 | Buttermann ............. | 623/17.13 |

(Continued)

OTHER PUBLICATIONS

"Implantable Multichannel Telemetry System," Abstracts from Biomechanics Laboratory.

(Continued)

*Primary Examiner*—Paul Prebilic
(74) *Attorney, Agent, or Firm*—Steven M. Koehler; Westman, Champlin & Kelly, P.A.

(57) ABSTRACT

A prosthesis includes a first plate and a second plate spaced apart from the first plate to form a gap therebetween. The second plate can move independently of the first plate. The prosthesis also includes a lower plate spaced apart from the first plate and the second plate. A plurality of support posts support the first plate and the second plate above the lower plate.

26 Claims, 22 Drawing Sheets

U.S. PATENT DOCUMENTS

| | | | |
|---|---|---|---|
| 5,879,394 A * | 3/1999 | Ashby et al. | 623/20.33 |
| 5,957,979 A * | 9/1999 | Beckman et al. | 623/20.33 |
| 6,034,296 A * | 3/2000 | Elvin et al. | 623/16.11 |
| 6,296,664 B1 | 10/2001 | Middleton | 623/17.15 |
| 6,299,646 B1 * | 10/2001 | Chambat et al. | 623/20.33 |
| 6,315,797 B1 | 11/2001 | Middleton | 623/17.16 |
| 6,395,035 B2 | 5/2002 | Bresina et al. | 623/17.15 |
| 6,607,559 B2 | 8/2003 | Ralph et al. | 623/17.16 |
| 7,066,959 B2 | 6/2006 | Errico et al. | 623/17.14 |
| 7,179,294 B2 * | 2/2007 | Eisermann et al. | 623/17.15 |
| 2002/0035400 A1 | 3/2002 | Bryan et al. | 623/17.15 |
| 2004/0054411 A1 * | 3/2004 | Kelly et al. | 623/17.13 |
| 2004/0158326 A1 | 8/2004 | Ralph et al. | 623/17.11 |
| 2004/0167626 A1 | 8/2004 | Geremakis et al. | 623/17.15 |

OTHER PUBLICATIONS

Taylor, S.J.G. & Walker, P.S. "Forces and Moments Telemetered from Two Distal Femoral Replacements during Various Activities," *Journal of Biomechanics*, 2001, pp. 839-848.

* cited by examiner

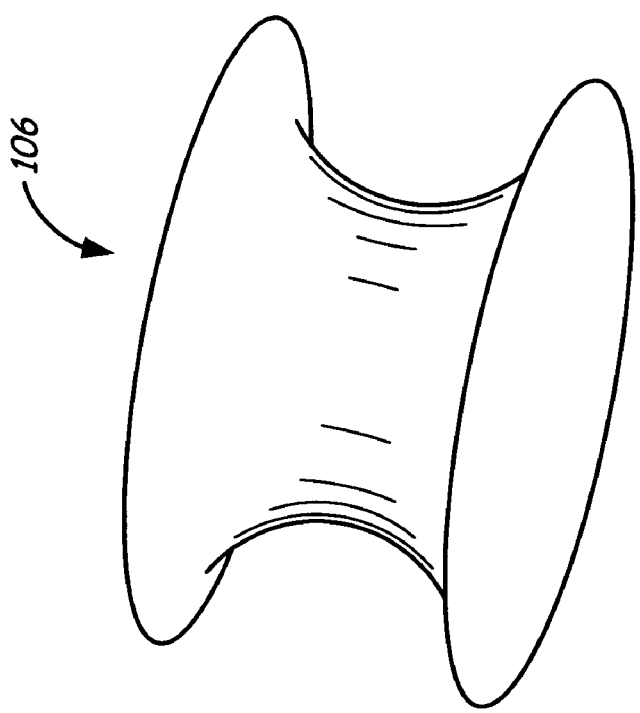
FIG. 13
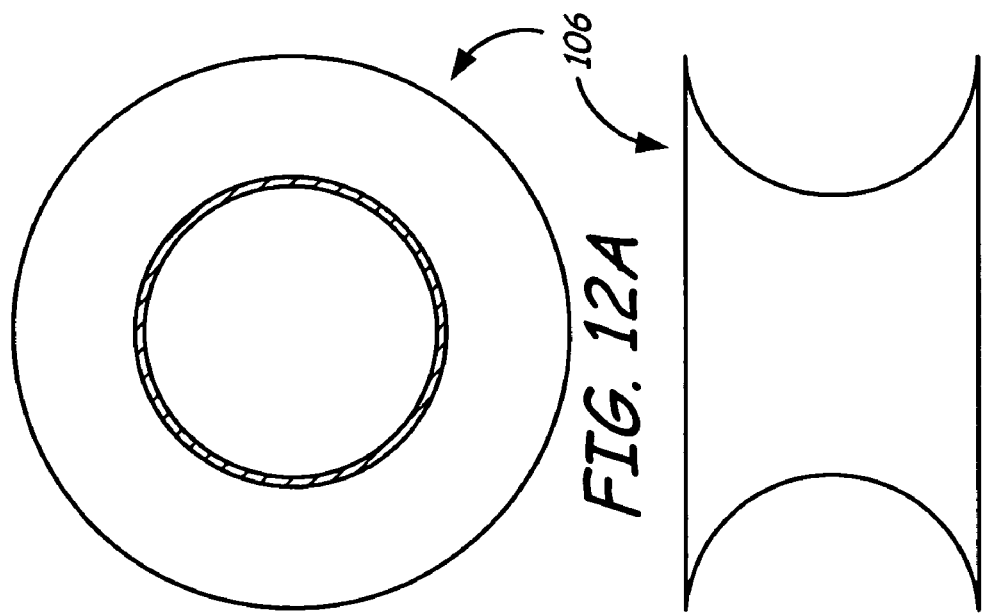
FIG. 12A
FIG. 12B

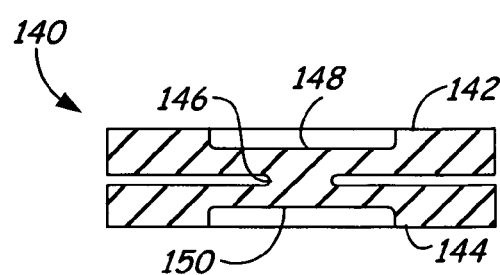
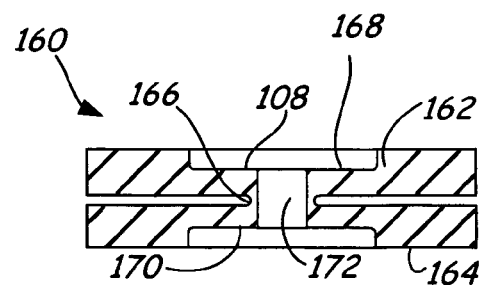
FIG. 16
FIG. 18
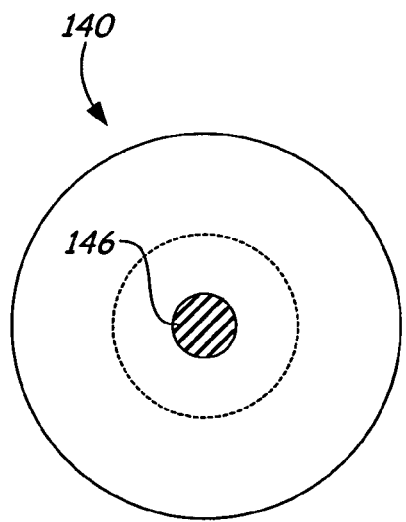
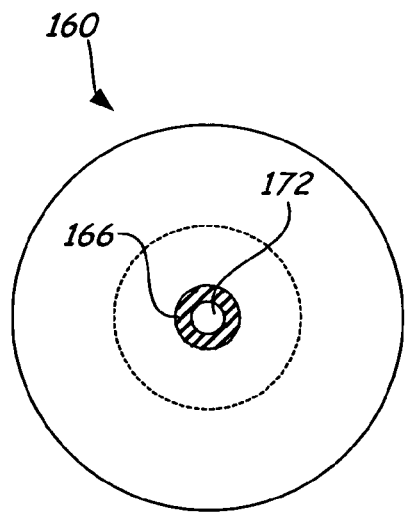
FIG. 17
FIG. 19

DUAL-TRAY PROSTHESIS

CROSS REFERENCE TO RELATED APPLICATIONS

The present application is a continuation of application of U.S. patent application Ser. No. 11/002,340, filed Dec. 2, 2004 now U.S. Pat. No. 7,179,295, which claims benefit of U.S. provisional patent application having Ser. No. 60/526,728, filed Dec. 3, 2003, and is also a continuation-in-part of U.S. patent application Ser. Nos. 10/431,206 (now abandoned) and 10/431,207 (now abandoned), both filed May 7, 2003, each of which is a continuation-in-part of U.S. patent application Ser. No. 09/972,074 (now abandoned), filed Oct. 5, 2001; the contents of the aforementioned applications are hereby incorporated by reference in their entirety.

BACKGROUND OF THE INVENTION

The present invention pertains generally to a joint prosthesis. In particular, the present invention relates to absorbing forces in a joint prosthesis.

The human body includes several joints such as the knee, the hip, the shoulder and the elbow. These joints are vulnerable to damage from various injuries, wear and disease. When the joints have been severely damaged, partial or total joint replacement may be the only viable solution. In many joint replacements, a prosthetic structure is inserted into the joint. Typically, the prosthetics include a base member secured to a bone to allow normal joint articulation.

The human knee is the single largest joint of the human body, but due to its structure, is arguably the most vulnerable to damage. The leg consists principally of a lower bone called a tibia and an upper bone known as the femur. The tibia and femur are hinged together at the knee joint. The knee joint includes several femoral condyles supported in an engagement with crescentic fibrocartilages that are positioned on the upper end of the tibia and receive the femur. The joint is held together by numerous ligaments, muscles and tendons. The patella is a similarly supported bone positioned in front of the knee joint and acts as a shield for it.

In addition to providing mobility, the knee plays a major role in supporting the body during static and dynamic activities. The knee works in conjunction with the hip and ankle to support the body weight during static erect posture. The knee is also heavily loaded because of its location connecting the two longest bones in the human body. Body weight, inertia and ground reaction forces often produce large moments at the knee. Dynamically, the knee joint must transmit extremely high forces needed for powerful movement of the lower extremity, while damping out impulsive shock loads to the spine and head. Furthermore, the knee must provide major stability to the lower extremity as well as fulfill major mobility roles during movement.

In current knee replacement prosthetic designs, the tibia is resected to form a flat, horizontal platform known as a tibial plateau. A tibial platform is secured to the tibial plateau with posts or anchors fixed normal or perpendicular to the tibia plateau. The anchors provide additional support to the tibial platform when the joint is subjected to shear, tipping and torque forces present under normal knee articulation.

A similar component, comprising a curved convex semi-spherical shell, covers the femoral condyles and slidably engages a concave tibial bearing insert. On a side opposite the femoral component, the tibial insert is substantially flat and slidably engages the tibial platform. Interaction of opposing surfaces of these three elements, the femoral component, the tibial component, the tibial insert and the tibial platform allows the prostheses to function in a manner equivalent to a natural knee joint.

Current prosthetic designs are relatively inflexible and inelastic, especially when reacting to forces produced on the knee joint. When a prosthesis is placed in-vivo, the prosthesis experiences a larger number of force cycles that can ultimately lead to failure of the prosthesis. As a result, a prosthesis is needed that can absorb and limit failure over a larger number of force cycles.

SUMMARY OF THE INVENTION

A prosthesis includes a first plate and a second plate spaced apart from the first plate to form a gap therebetween. The second plate can move independently of the first plate. The prosthesis also includes a lower plate spaced apart from the first plate and the second plate. A plurality of support posts support the first plate and the second plate above the lower plate.

BRIEF DESCRIPTION OF THE DRAWINGS

FIGS. 12A-12B illustrate a top sectional view and a side sectional view of a round post in a shock absorber.

FIG. 13 is a perspective view of a round post in a shock absorber.

FIGS. 14-27 illustrate exemplary embodiments of shock absorbers that can be integrated into a prosthetic structure.

DETAILED DESCRIPTION OF THE PREFERRED EMBODIMENTS

An exemplary prosthetic according to the present invention will now be described. Generally, a prosthetic includes a component mounted to the femur 2 and another component mounted to the tibia 4. Both femur 2 and tibia 4 are shown in dotted lines in FIG. 1. Although described with reference to a knee, those skilled in the art will recognize applicability of the present invention to other prosthetic structures.

Figure 1:
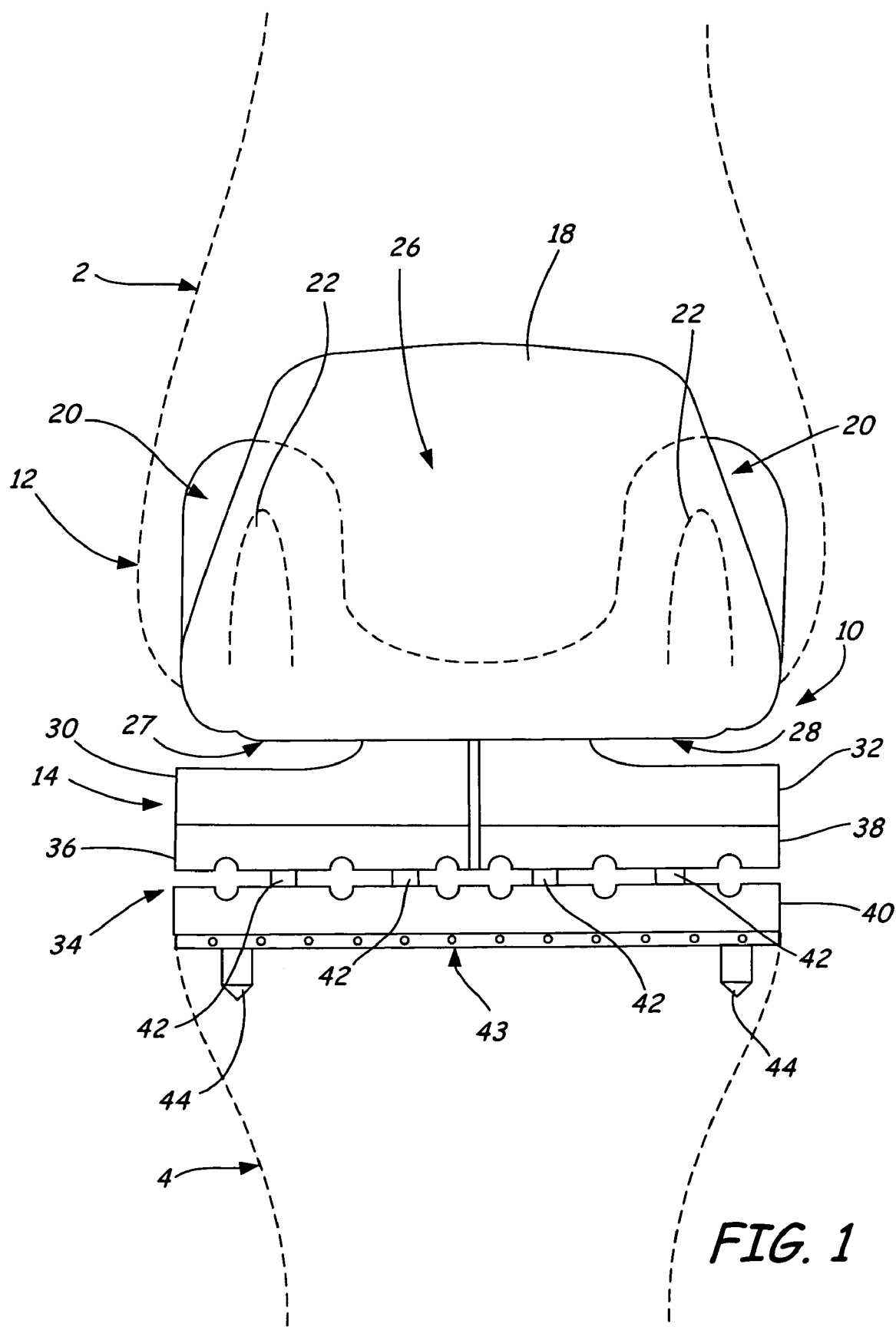
FIG. 1 is a front view of a knee prosthesis according to the present invention.

FIG. 1 further illustrates assembly 10 in accordance with an exemplary embodiment of the present invention. Assembly 10 includes femoral component 12 mounted to the femur 2 and tibial component 14 mounted to the tibia 4. Femoral component 12 includes flange 18 formed integrally with two condyles 20. Femoral component 12 includes fixing posts or anchors 22 integrally formed on femoral component 12. Posts 22 are used to fix the femoral component 12 to femur 2.

An outside surface 26 of flange 18 provides most of the bearing surface for a patella, not shown, which cooperates with femur 2 to protect the joint. Condyles 20 are provided for replacing the condylar surfaces of femur 2 and include medial condylar surface 27 and lateral condylar surface 28.

Tibial component 14 includes tibial inserts 30 and 32 and body portion 34. Medial tibial insert 30 is adapted to engage medial condylar surface 27, while lateral tibial insert 32 is adapted to engage lateral condylar surface 28. The medial and lateral condylar surfaces 27 and 28 exert force on medial tibial insert 30 and lateral tibial insert 32, respectively. Medial and lateral inserts 30 and 32 can be made from polyethylene or any other suitable material.

During articulation of the knee joint, inserts 30 and 32 exert forces on body portion 34. Body portion 34 includes medial plateau (or plate) 36, lateral plateau (or plate) 38 and lower plate 40. Support posts 42 support the medial plateau 36 and lateral plateau 38. In one embodiment, body portion 34 serves as a transducer for measuring force articulated within the knee joint. In this embodiment, strain gauges are mounted directly below support post 42 and sense strain therein. When installed as a replacement assembly for a natural human knee joint, assembly 10 provides quantitative feedback in force load balance across the tibial-femoral joint. Tibial component 14 also includes a cover plate 43 secured to lower plate 40 and fixing posts or anchors 44 to secure tibial component 14 to tibia 4. In one embodiment, cover plate 43 is welded to lower plate 40.

Figure 2:
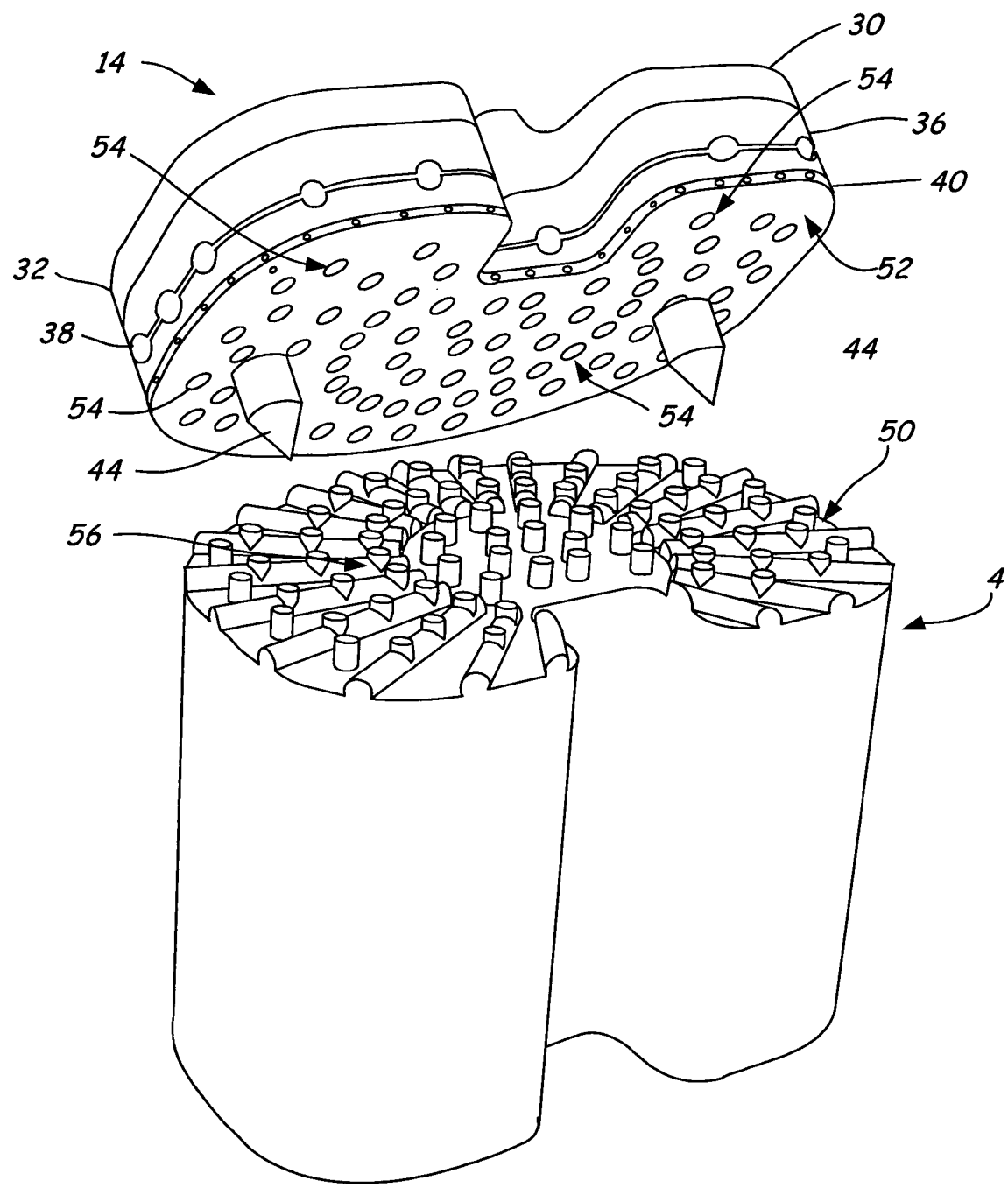
FIG. 2 is an isometric perspective view of a tibia and a tibial component.
Figure 3:
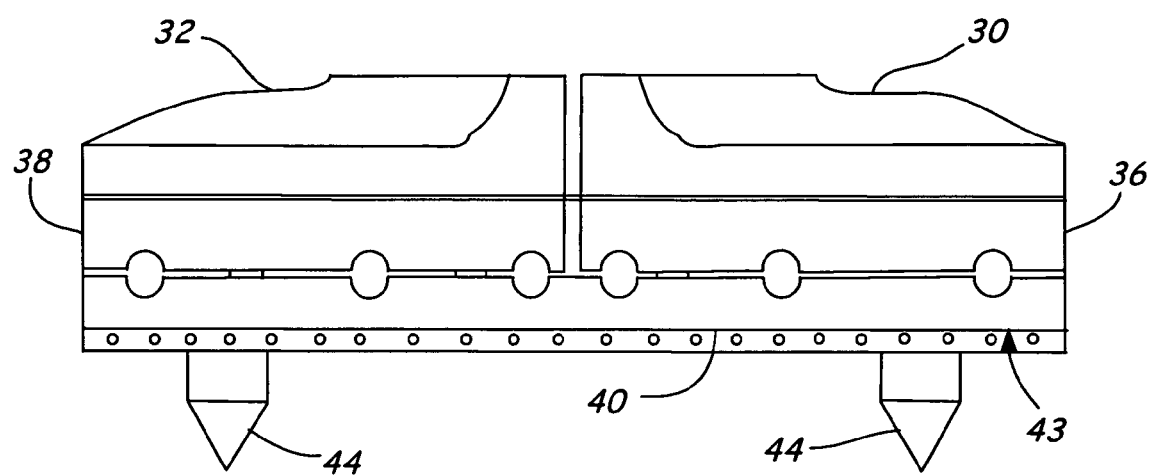
FIG. 3 is a front view of a tibial component.
Figure 4:
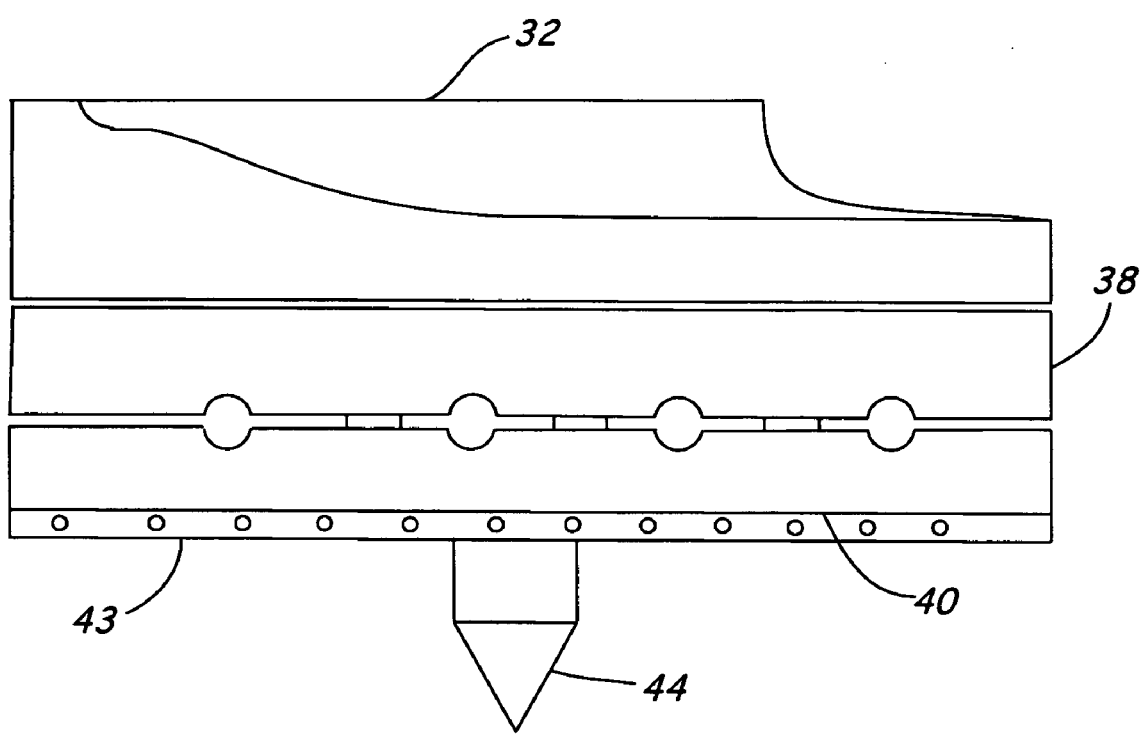
FIG. 4 is a side view of a tibial component.

FIG. 2 illustrates a perspective view of tibial component 14 and tibia 4. Tibia 4 has been resected (generally flat) to form a plateau 50. Cover plate 43 includes a major surface 52 adapted to engage plateau 50 of tibia 4. In the embodiment illustrated, major surface 52 can include a plurality of apertures 54. The plurality of apertures 54 are connected to passageways and are disposed substantially throughout major surface 52 in order to enable growth of soft tissue, blood vessels, nerves, etc. from tibia 4 through the passageways in lower plate 40. A number of different configurations and quantity of apertures may be used. In one embodiment, the plurality of apertures is at least ten apertures, and other embodiments include at least twenty-five and fifty apertures. The growth is schematically indicated on plateau 50 at 56 as surface variations.

The design of body portion 34 provides several advantages. The various components of body portion 34 are elastic and act to dampen forces placed throughout the joint. Additionally, tibial component 14, since apertures in cover plate 43 provides an infusion of growth to the structure of body portion 34, is more acceptable to the body. Additionally, only small fixing posts 44 are necessary in order to secure tibial component 14 to tibia 4 prior to infusion. In prior art embodiments, a large center stem was necessary to secure tibial components to respective tibias. The large center stem was particularly invasive to the body, which yielded an undesirable situation. Furthermore, soft tissue growth through lower plate 40 provides additional damping for the knee joint. When pressure is placed on tibial component 14, the soft tissue growth acts to dampen these forces, in particular it minimizes shear forces on the knee joint. The soft tissue growth provides not only a more natural scenario, but can protect the knee joint from further failure. A further advantage in that weight of tibial component 14 is reduced by 35% over prior art components, in one embodiment.

Figure 5:
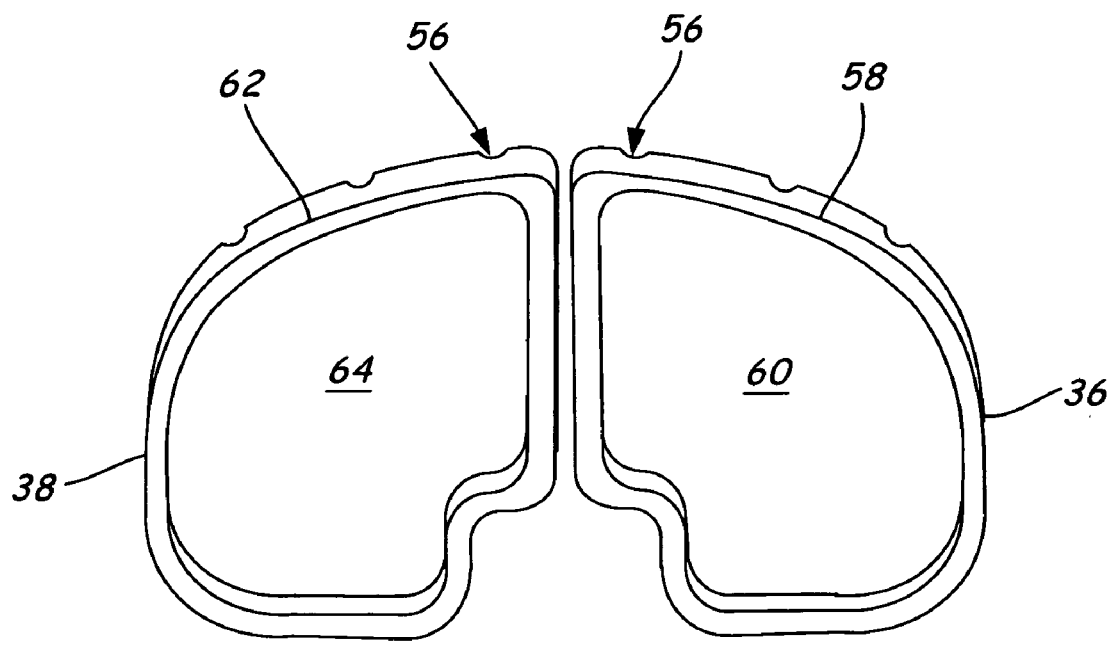
FIG. 5 is a top perspective view of a medial plateau and a lateral plateau.
Figure 6:
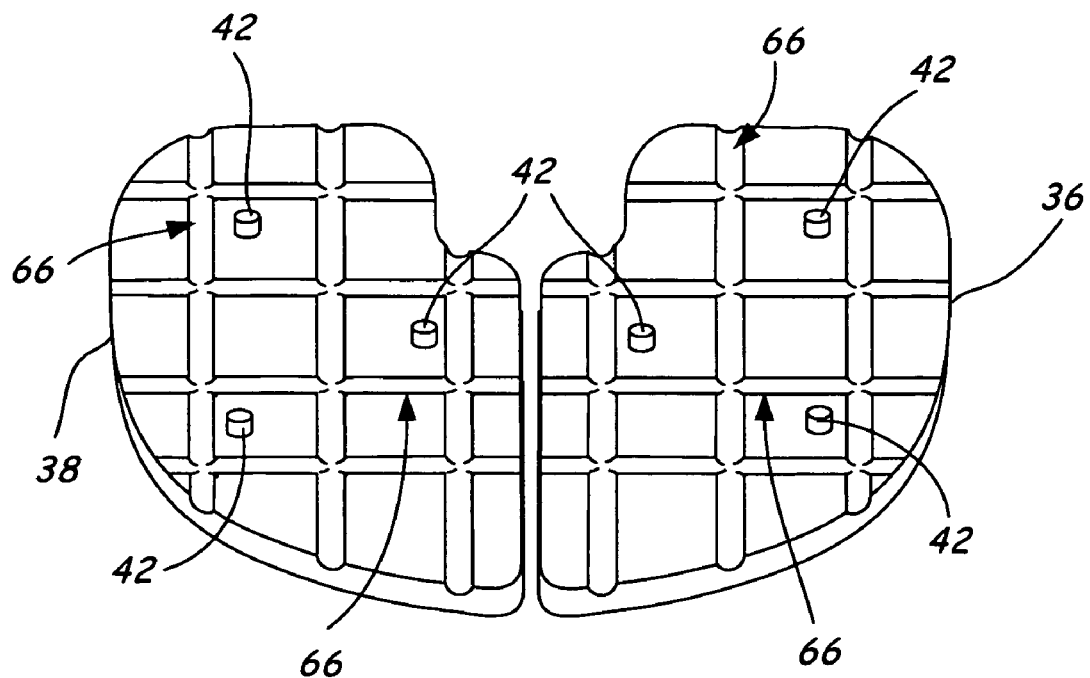
FIG. 6 is a bottom perspective view of a medial plateau and a lateral plateau.

FIGS. 3-9 illustrate various views of portions of tibial component 14. FIGS. 5-6 illustrate medial plateau 36 and lateral plateau 38. Medial plateau 36 and lateral plateau 38 receive medial tibial insert 30 and lateral tibia insert 32, respectively. As appreciated by those skilled in the art, medial plateau 36 and lateral plateau 38 may be replaced with a single plateau in one embodiment. Medial plateau 36 includes a wall 58 defining a cavity 60 and lateral plateau 38 includes a wall 62 defining a cavity 64. Walls 58 and 62 extend around the circumference of medial plateau 36 and lateral plateau 38 to receive the medial insert 30 and tibial insert 32, respectively.

Medial plateau 36 and lateral plateau 38 are spaced apart to isolate forces from medial insert 30 and tibial insert 32, respectively. As shown in FIG. 6, support posts 42 are cylindrical (round), particularly at their coupling to the plateaus 36, 38 and plate 40, and support the medial plateau 36 and lateral plateau 38 to space the plates apart from lower plate 40. The cylindrical posts 42 aid in extending the life of the prosthesis, but other curved shapes of posts so as to minimize stress concentration may be used. For each of the medial plate 36 and lateral plate 38, support posts 42 include three individual posts arranged in an isosceles triangle configuration. The configuration of support posts 42 allows body portion 34 to closely resemble the natural configuration of the mechanics of the knee during articulation and provide added stability. The support posts 42 are also responsive to shear and torsion forces acting on the medial plateau 36 and lateral plateau 38 that are caused by various joint movements. Other configurations of support posts may also be used.

Each of the bottom surfaces of medial plateau 36 and lateral plateau 38 can include a plurality of grooves 66. In the illustrated embodiment, the plurality of grooves 66 extend in both a lateral direction and longitudinal direction across the bottom surface of medial plateau 36 and lateral plateau 38. The plurality of grooves 66 accommodates the growth of soft tissue, blood vessels, nerves, etc. from tibia 4 between medial plateau 36 and lateral plateau 38 and lower plate 40. Although herein illustrated wherein the plurality of grooves 66 extend in lateral and longitudinal directions, various other groove configurations may be used in accordance with the present invention on the knee prosthesis or other joint prostheses.

Figure 7:
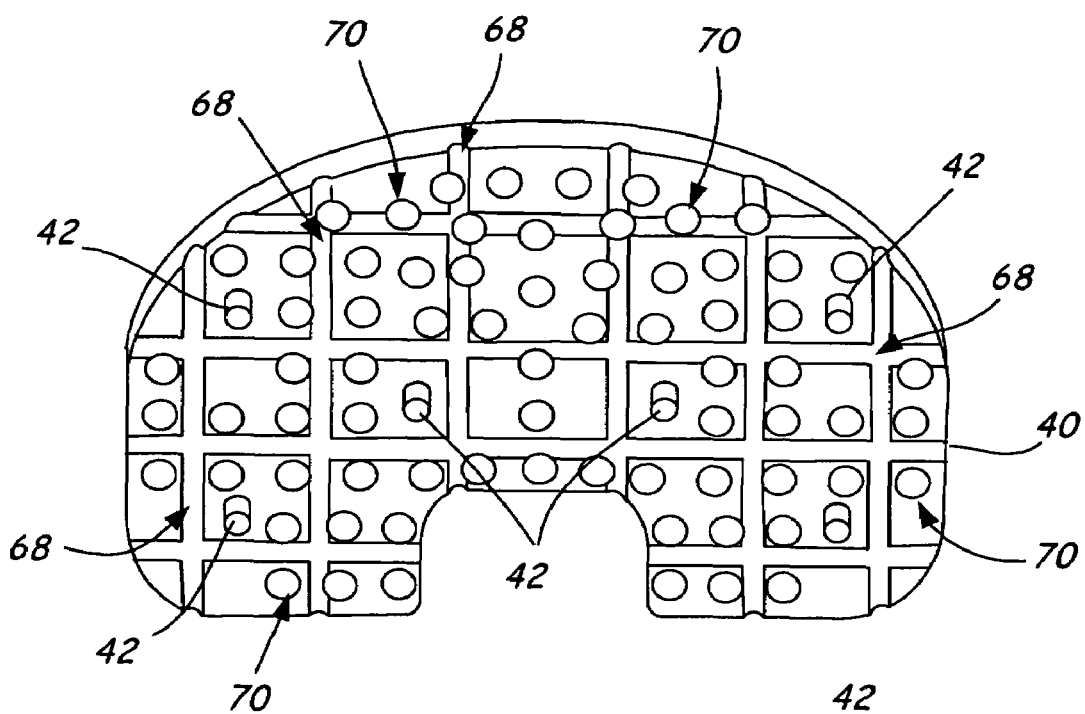
FIG. 7 is a top perspective view of a lower plate of a body portion.
Figure 8:
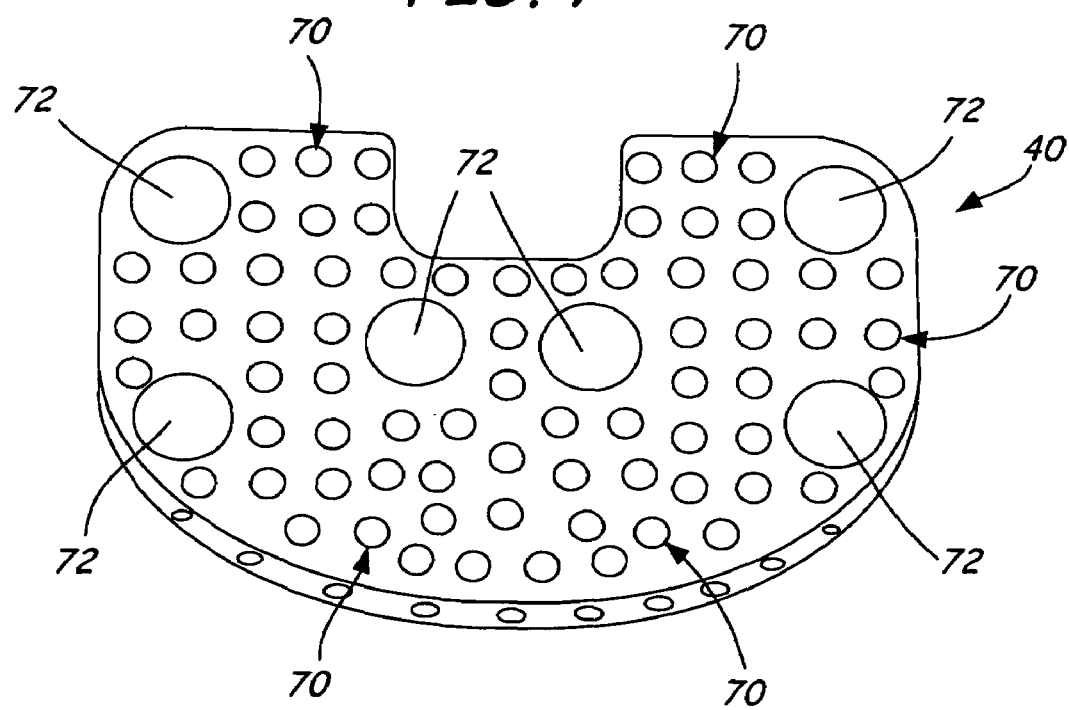
FIG. 8 is a bottom perspective view of a lower plate of a body portion.

FIGS. 7 and 8 illustrate views of lower plate 40. As illustrated in FIG. 7, the upper surface of lower plate 40 can include a plurality of grooves 68 extending in lateral and longitudinal directions on the top surface of lower plate 40. In one embodiment, the plurality of grooves 68 of lower plate 40 are aligned with the plurality of grooves 66 of medial plateau 36 and lateral plateau 38. In addition to the plurality of grooves, a plurality of apertures 70 extending normal to the top surface of lower plate 40 are provided throughout lower plate 40. Both the plurality of grooves 68 and plurality of apertures 70 are configured to accommodate growth from tibia 4.

FIG. 8 illustrates a bottom perspective view of lower plate 40. The plurality of apertures 70 are shown to extend through the lower plate 40. A plurality of cavities 72 are further provided directly below support post 42. Each of the cavities 72 serve as flexure members that dampen forces placed on lower plate 40 by support posts 42. The flexure members 72 are deflected when forces are placed on support posts 42, which acts to dampen the forces and provide a more elastic prosthetic structure.

Figure 9:
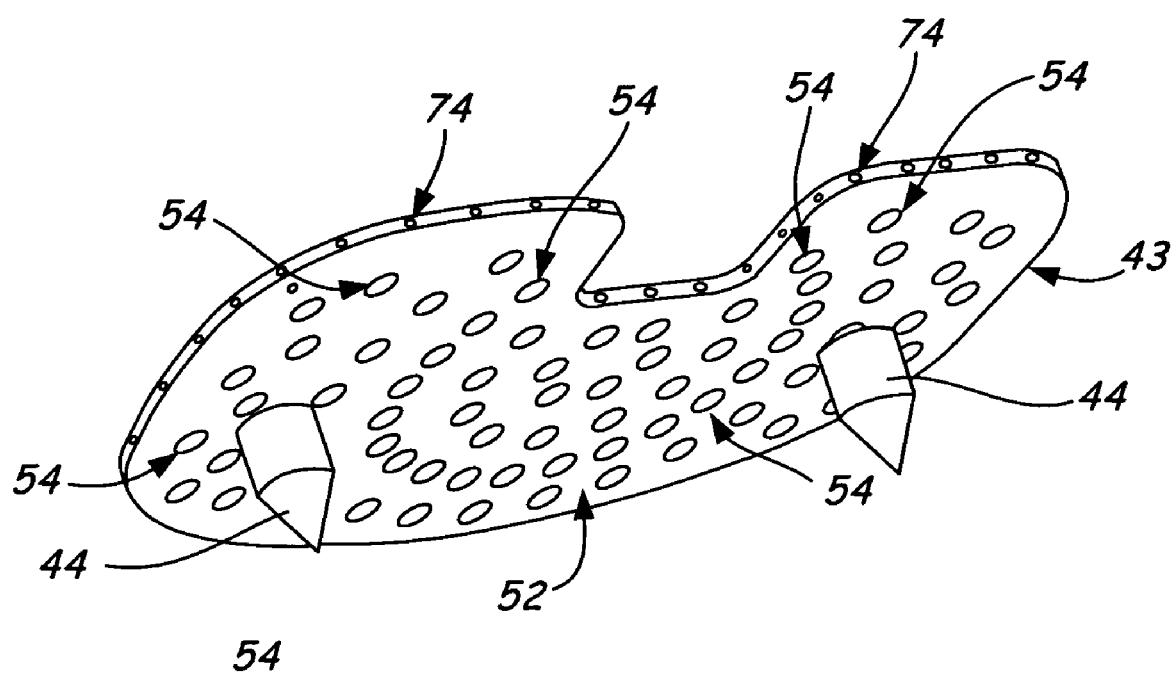
FIG. 9 is a bottom perspective view of a cover plate.

As illustrated in FIG. 9, major surface 52 of cover plate 43 includes a plurality of apertures 54 disposed substantially about the entire major surface. Cover plate 43 is secured to tibia 4, which provides additional elasticity to the prosthesis with respect to compressive, shear and torsion loads. The plurality of apertures 54 are substantially perpendicular to the major surface and extend through cover plate 43. In the embodiment illustrated, a plurality of apertures 56 are also provided about a periphery of cover plate 43 on a surface substantially perpendicular to the major surface. The plurality of apertures 74 extends radially outwardly but may be of any configuration. These plurality of apertures are connected to passageways that further allow growth of tissue from tibia 4 through cover plate 43. Various aperture configurations can be used.

The prosthetic structure described above is designed to provide an elastic structure that in one embodiment can also accommodate tissue, vessels and nerve growth into the structure. The structure acts to dampen forces placed throughout the implant. Each of the separate components are elastic, which contribute to the overall elasticity of the structure. The medial and lateral inserts together with the medial and lateral plateaus respond to static and dynamic loads independently and serve to dampen forces from the femur. The round posts supporting the medial and lateral plateaus are associated with flexures that deflect under load, which ultimately diminishes vertical stiffness of the structure. Soft tissue, blood vessel and nerve growth infuse into and around apertures in a cover plate and lower plate in order to further provide an elastic structure that will dampen forces placed on the prosthetic implant. By dampening the forces placed on the prosthetic structure, loads, and particularly impact loads, placed on the knee joint and other joints in the body are reduced.

An aspect of the present invention involves integrating a shock absorber into a prosthetic structure such as described above. The embodiments described below can be integrated into the prosthetic structure in different ways including substituting the absorbers for elements described above and adding absorbers to the prosthetic structure. The shock absorber acts to dampen forces placed upon the prosthetic structure to provide elasticity, which is helpful in maintaining durability for prosthetic structures that experience numerous force cycles throughout the life of the prosthetic structure.

Figure 10:
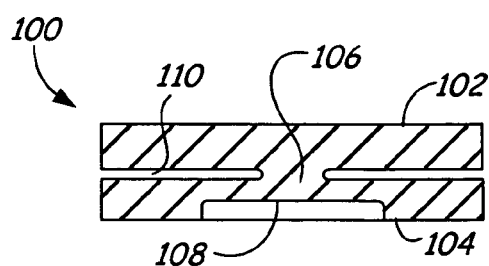
FIGS. 10-11 illustrate an exemplary embodiment of a shock absorber that can be integrated into a prosthetic structure.
Figure 11:
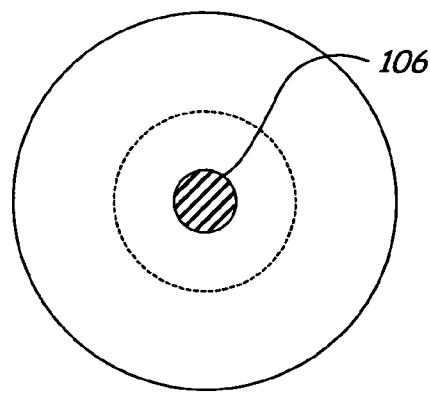

FIGS. 10 and 11 illustrate one embodiment of a prosthetic shock absorber that may be integrated into a prosthetic structure. Shock absorber 100 includes a first plate 102 and a second plate 104 spaced apart from first plate 102. A post 106 is provided between first plate 102 and second plate 104. In one embodiment, post 106 is substantially round, particularly at its connection to the first plate 102 and second plate 104. The first plate 102, second plate 104 and post 106 form an integral structure. Shock absorber 100 may be machined using a technique such as electrical discharge machining (EDM) to form post 106. Andrew Tool Company, located at 2405 Annapolis Lane, #266, Plymouth, Minn. 55441 can provide such machining techniques. It is believed this process includes initially machining square posts using the EDM wire process. Then, using small or thin shaped electrodes, the corners are evaporated to form a substantially round post. The electrode process may be a two-step process, one side (e.g. semi-circular) of the post at a time. The manufacturing of post 106 may cause fillets to be formed in post 106 proximate first plate 102 and second plate 104. These fillets can act to distribute stress on the plates 102 and 104. Lower plate 104 also includes a flexure 108 positioned to provide additional damping for shock absorber 100.

FIGS. 12A, 12B and 13 further illustrate post 106. The post 106 forms a radius that minimizes structural stress and optimizes electro-mechanical performance. As a result of the machining of post 106, a gap 110 is formed between first plate 102 and second plate 104. An exemplary gap 110 can be in a range of about 0.04 to about 0.5 inches, although forming substantially round posts as described above in a prosthesis with any gap and a flexure comprises an aspect of the present invention. Furthermore such a prosthesis with a gap less than 0.06 inches is particularly advantageous. In another embodiment, a gap of 0.04 inches is used. It should also be noted that the gap may vary depending upon the type of material used and quality and/or accuracy of the machining process. Some suitable materials include, but are not limited to, bio-compatible materials such as titanium and cobalt.

Figure 14:
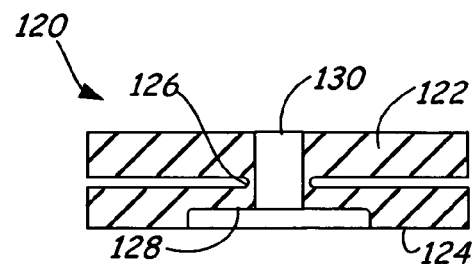
Figure 15:
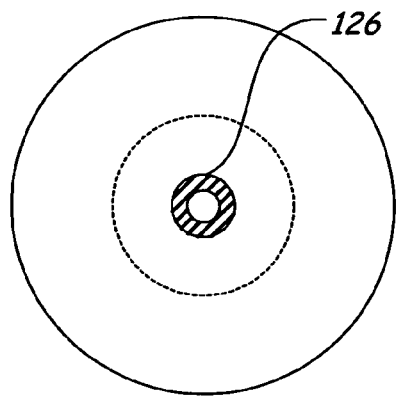

FIGS. 14 and 15 illustrate another embodiment of shock absorber 120 in accordance with an aspect of the present invention. Absorber 120 includes a first plate 122, a second plate 124, a post 126 and a flexure 128. Post 126 and the posts described below in further embodiments are made substantially round, at least at their connection to other components such as plates and flexures, in a manner as described above in the previous embodiments. In this embodiment, post 126 is hollow. Hollow post 126 forms a cavity 130. In a further embodiment, additional damping may be provided by filling cavity 130 with a substance. Example substances include oil, gel and a liquid material. Cavity 130 may then be sealed to prevent the substance within cavity 130 from leaking.

FIGS. 16 and 17 illustrate yet another embodiment of a shock absorber 140 including a first plate 142, a second plate 144 and a post 146. In this embodiment, first plate 142 includes a first flexure 148 and second plate 144 includes a second flexure 150 to provide additional damping.

FIGS. 18 and 19 illustrate a shock absorber 160 similar to shock absorber 140 illustrated in FIGS. 16 and 17. Shock absorber 160 includes first plate 162, second plate 164, post 166, first flexure 168 and second flexure 170. Additionally, post 166 is hollow and forms a cavity 172. As discussed earlier, cavity 172 can be filled with a substance such as oil, gel and/or a liquid material and sealed to provide additional damping.

Figure 20:
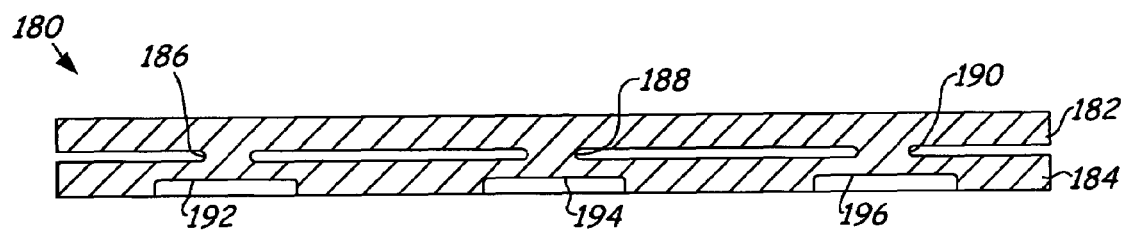

The absorbers described above can also be combined in series or parallel to provide added damping. FIG. 20 illustrates a shock absorber 180 that includes absorbing elements in parallel. Shock absorber includes a first plate 182 and a second plate 184. Substantially round posts 186, 188 and 190 separate first plate 182 and second plate 184. Flexures associated with posts 186, 199 and 190 provided in second plate 184 include flexures 192, 194 and 196, respectively.

Figure 21:
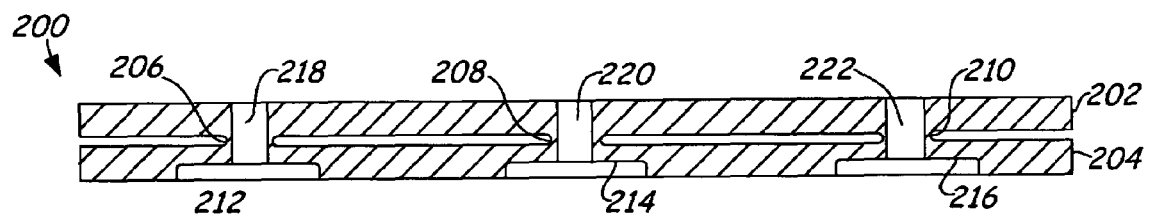

FIG. 21 illustrates shock absorber 200, which is similar to shock absorber 180 provided in FIG. 14. Absorber 200 includes first plate 202 and second plate 204. A plurality of posts, including post 206, post 208 and post 210 separate first plate 202 and second plate 204. Posts 206, 208 and 210 also include associated flexures 212, 214 and 216, respectively. In this embodiment, posts 206, 208 and 210 include cavities 218, 220 and 222 that may be filled with a substance as described above to provide additional damping.

Figure 22:
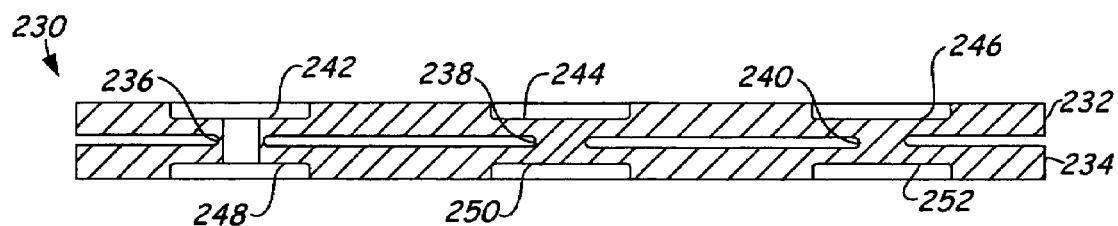

FIG. 22 illustrates another shock absorber 230. Absorber 230 includes a first plate 232 and a second plate 234. Absorber 230 also includes substantially round posts 236, 238 and 240. Each of first plate 232 and second plate 234 include flexures associated with posts 236, 238 and 240. First plate 232 includes flexures 242, 244 and 246 while second plate 234 includes flexures 248, 250 and 252.

Figure 23:
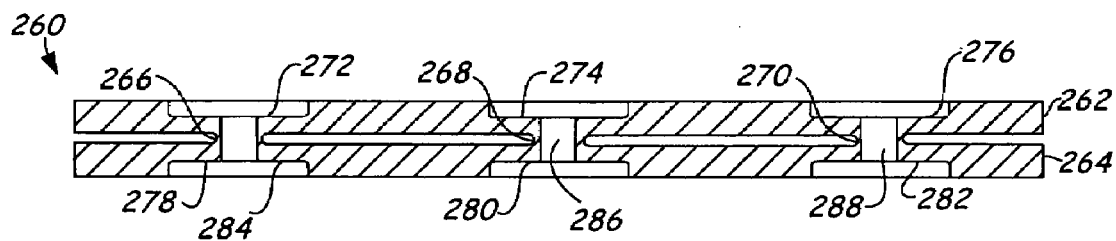

FIG. 23 illustrates another embodiment of a shock absorber 260. Absorber 260 includes first plate 262, second plate 264 and substantially round posts 266, 268 and 270. Plates 262 and 264 both include flexures associated with each of the posts 266, 268 and 270. First plate 262 includes flexures 272, 274 and 276 and second plate 264 includes flexures 278, 280 and 282. In this embodiment, posts 266, 268 and 270 are hollow to form cavities 284, 286 and 288, respectively. Cavities 284, 286 and 288 may be filled with a substance to provide additional damping.

Figure 24:
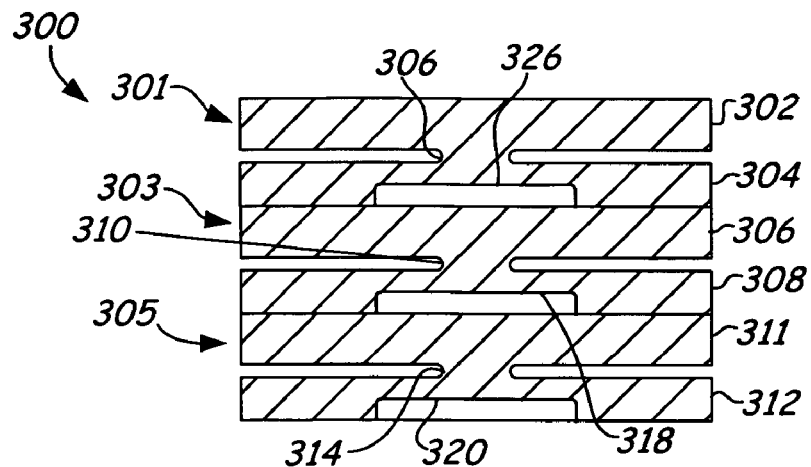

FIG. 24 illustrates another shock absorber 300 in accordance with another embodiment of the present invention. Absorber 300 includes absorbing elements 301, 303 and 305 arranged in series. Absorbing element 301 includes a first plate 302 and a second plate 304 separated by an associated post 306. Additionally, absorbing element 303 includes a first plate 306, a second plate 308 and a post 310. Absorbing element 305 includes a first plate 311 and a second plate 312 separated by an associated post 314. Additionally, plates 304, 308 and 312 include flexures 316, 318 and 320, respectively. Absorbing elements 301, 303 and 305 can be secured by welding or other suitable means.

Figure 25:
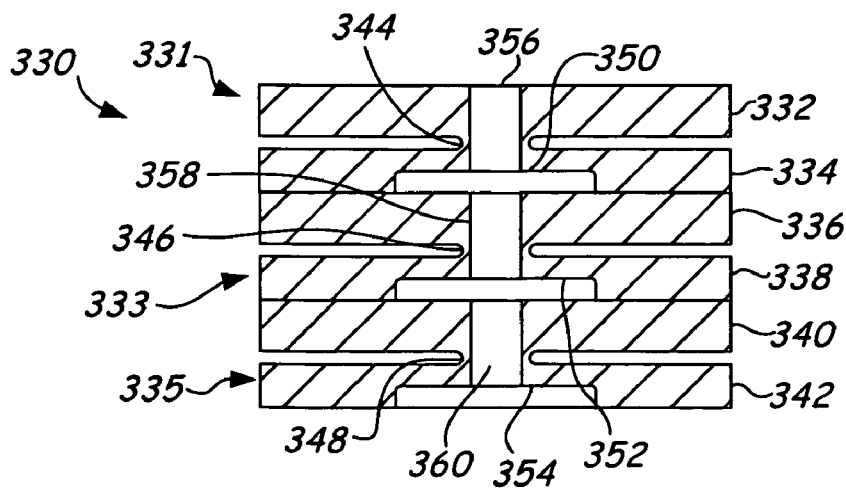

FIG. 25 provides a similar embodiment to absorber 300 illustrated in FIG. 18. In this embodiment, absorber 330 includes absorbing elements 331, 333 and 335. Absorbing element 331 includes plates 332 and 334. Element 333 includes plates 336 and 338 and element 335 includes plates 340 and 342. Additionally, posts 344, 346 and 348 are provided in absorbing elements 331, 333 and 335, respectively. Flexures 350, 352, and 354 are also provided in absorbing elements 331, 333 and 335, respectively. In this embodiment, posts 344, 346 and 348 are hollow and form cavities 356, 358 and 360, respectively, which can be filled with a suitable substance for additional damping.

Figure 26:
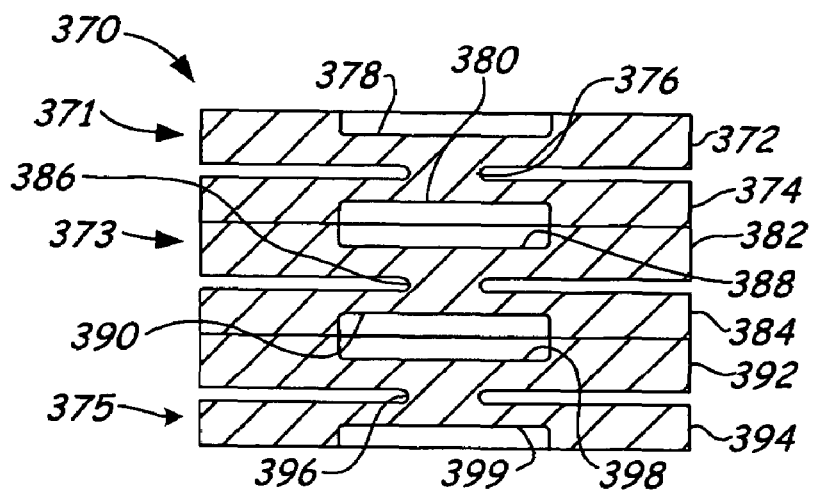
Figure 27:
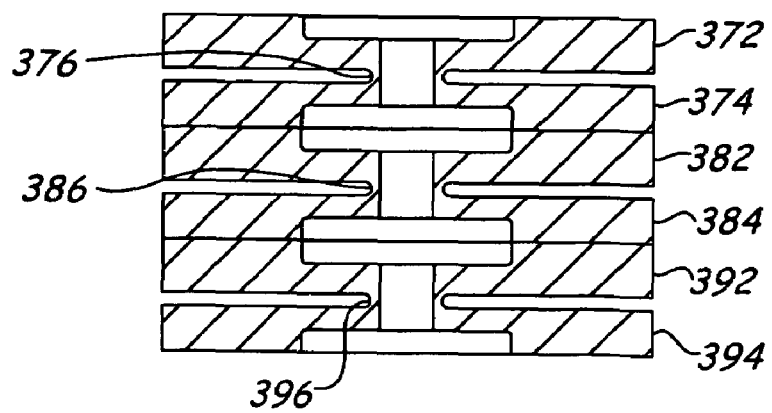

FIGS. 26 and 27 illustrate similar absorbers to those illustrated in FIGS. 24 and 25, respectively. In the embodiment illustrated in FIG. 26, absorber 370 includes absorbing elements 371, 373 and 375. Absorbing element 371 includes plates 372 and 374 spaced apart by substantially round post 376. Plates 372 and 374 include flexures 378 and 380, respectively. Absorbing elements 373 and 375 are similarly structured to absorbing element 371. Element 373 includes plates 382 and 384, post 386 and flexures 388 and 390, while element 375 includes plates 392 and 394, post 396 and flexures 398 and 399. In the embodiment illustrated in FIG. 27, each of the posts are hollow and form a cavity that may be filled with a suitable damping substance as described above.

As mentioned above, body portion 34 can be used as a force transducer to measure forces therein. FIGS. 28-32 illustrate an exemplary embodiment of a transducer according to the present invention. Transducer 400 is symmetrically u-shaped and constructed from suitable elastic material that is responsive to forces applied to medial and lateral plates 402 and 404. Ultimately, transducer 400 is used to measure forces present on the prosthetic components. The measurements can be used to properly align the components and analyze operation of the components.

Figure 28:
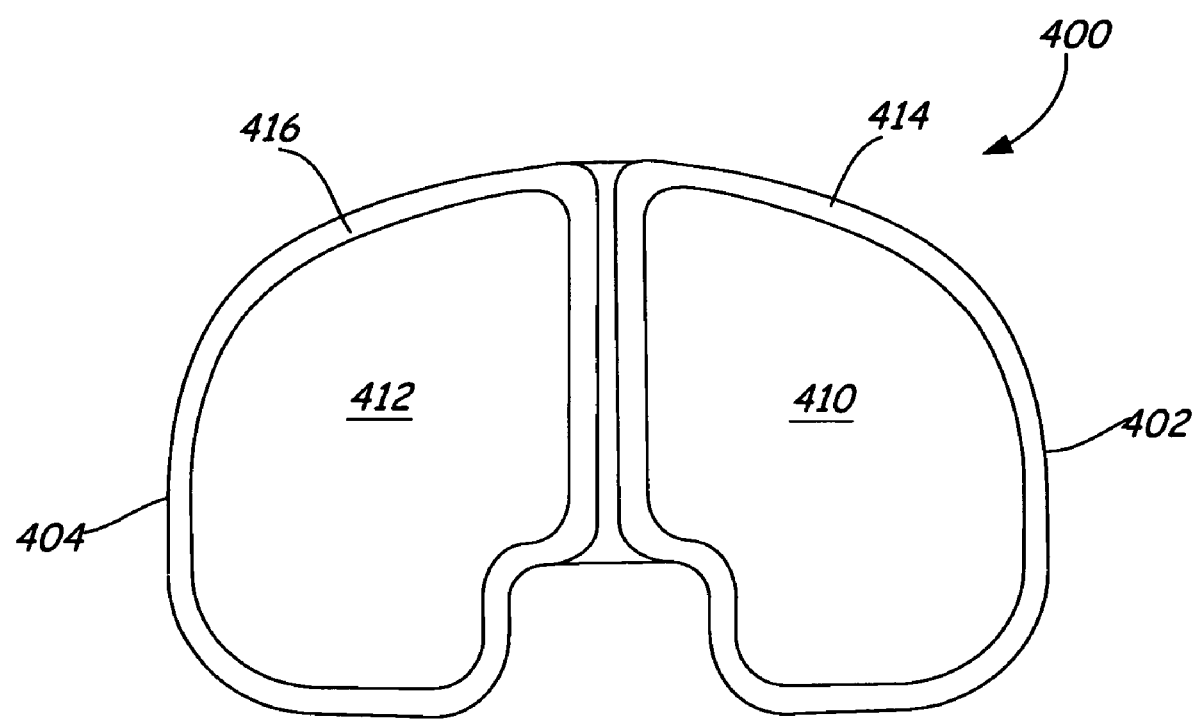
FIG. 28 is a top view of a transducer.

FIG. 28 illustrates a top view of transducer 400. Medial plate 402 and lateral plate 404 are spaced apart to isolate forces placed on medial and tibial inserts that can be positioned on medial plate 402 and lateral plate 404. Both medial plate 402 and lateral plate 404 include cavities 410 and 412 that cam receive tibial inserts. Walls 414 and 416 extend around the peripheral of plates 402 and 404 and define cavities 410 and 412.

Figure 29:
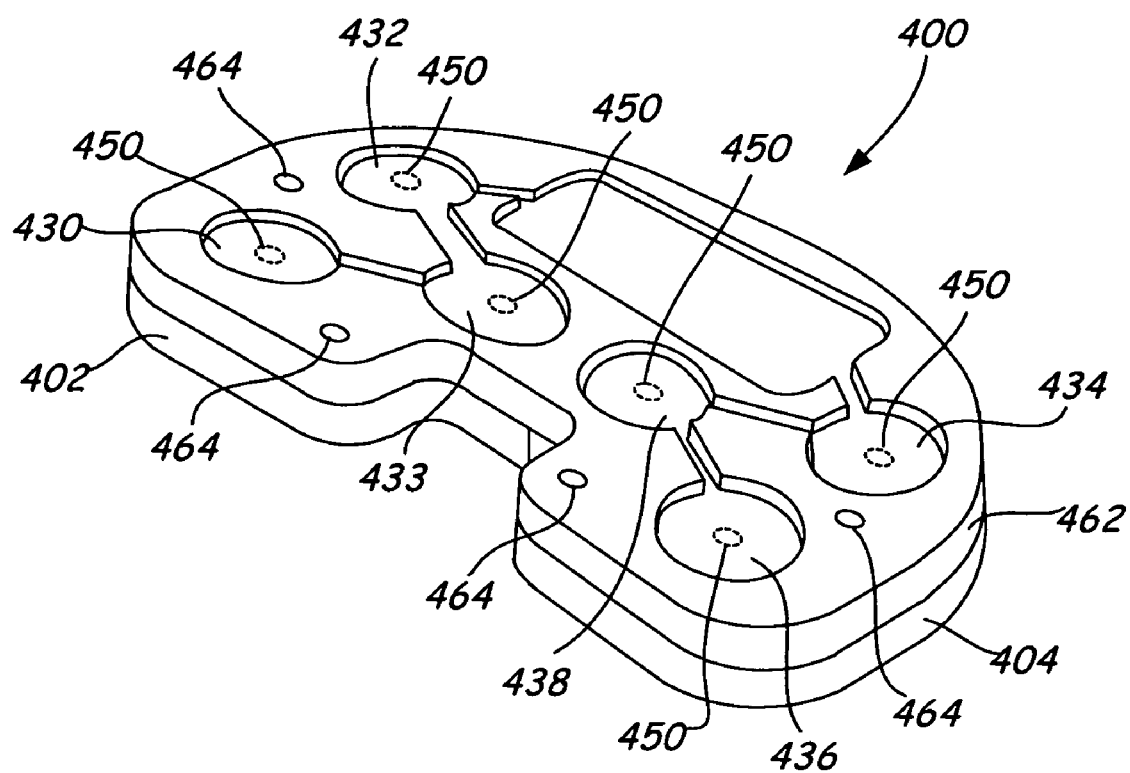
FIG. 29 is a bottom perspective view of a transducer.
Figure 30:
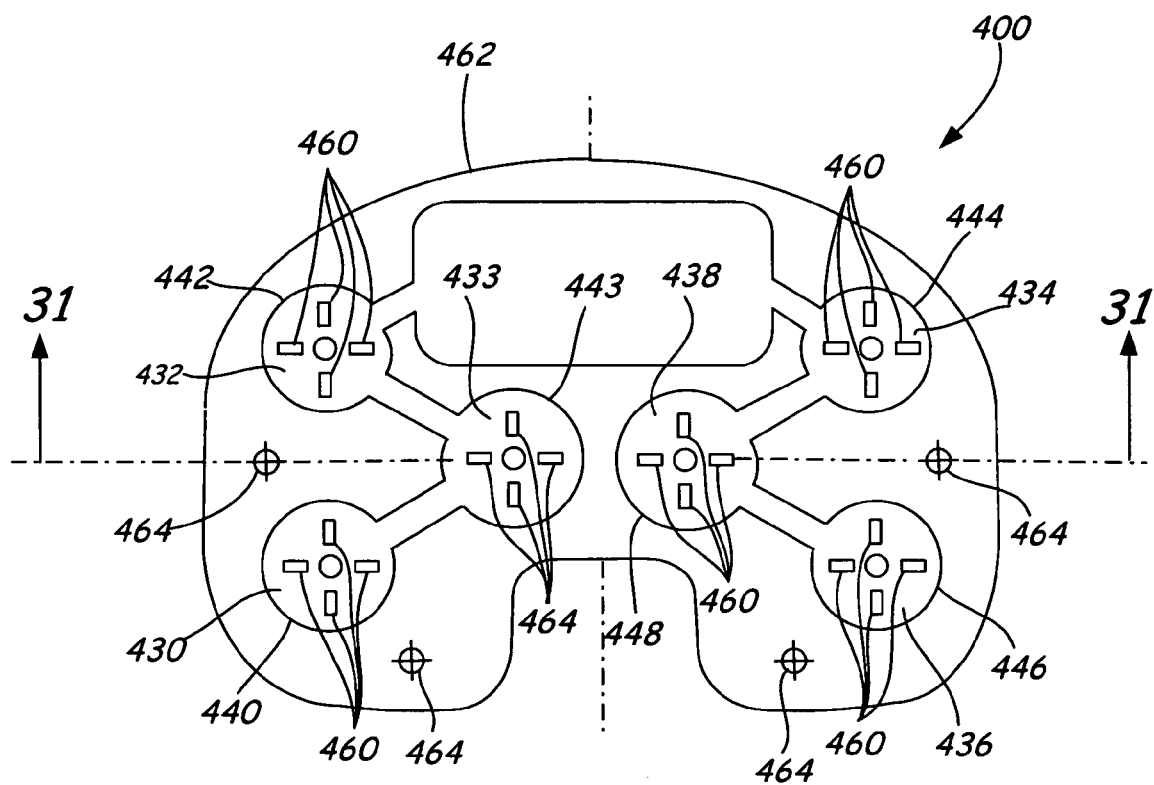
FIG. 30 is a bottom view of a transducer.
Figure 31:
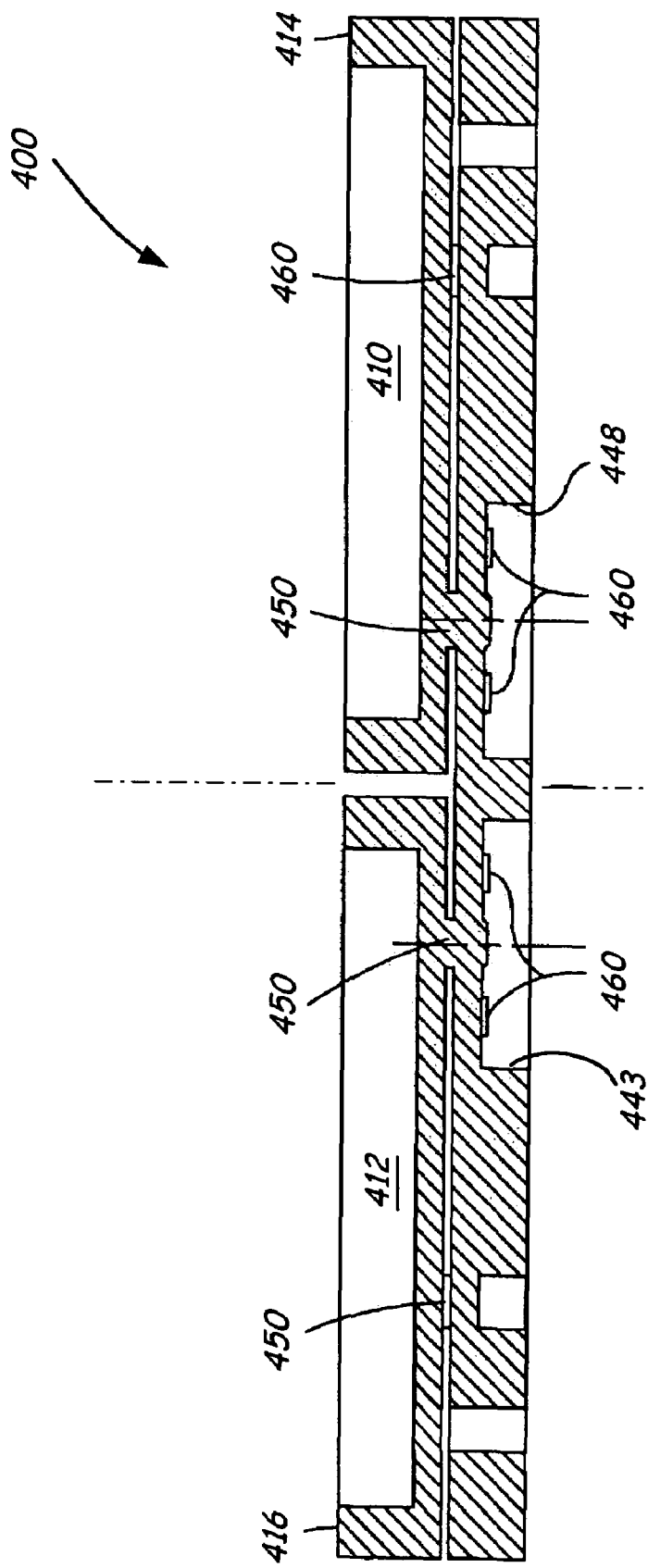
FIG. 31 is a cross sectional view of a transducer.

FIG. 29 illustrates a bottom perspective view of transducer 400 and FIG. 30 illustrates a bottom plan view of transducer 400. FIG. 31 illustrates a sectional of transducer 400 taken along line 31-31 in FIG. 30. As illustrated, lower plate 420 includes cavities 430, 432, 433, 434, 436 and 438, which define flexures 440, 442, 443, 434, 436 and 438, respectively. In the embodiment illustrated, cavities 430, 432, 433, 434, 436 and 438 are cylindrical with identical radii although other configurations may be used.

Forces applied to medial and lateral plates 402 and 404 are localized and directed through support posts 450 to a corresponding flexure member. Sensors 460 measures deflection of flexures 440, 442, 443, 434, 436 and 438 and can be resistive, capacitive, optical, etc. In the embodiment illustrated, a plurality of strain gauges are disposed in each respective cavity on a surface of each respective flexure member adjacent to support posts 450. Sensors 460 provide a quantitative response to forces reacted between the medial and lateral plates 402, 404 and lower plate 462, which correspond to forces carried by each of the condyles 20.

Flexures 440, 442, 443, 434, 436 and 438 allow forces to be measured throughout plate 402. Changes in forces can also be measured during articulation of the knee joint. Accordingly, an accurate replication of forces in a normal joint may be measured and analyzed. Incorrect loading on an artificial joint can cause damage to connecting tissues such as tendons and ligaments. Thus, by noticing incorrect loading, adjustments may be made within the prostheses to insure proper performance. Apertures 464 in lower plate 462 are provided for fasteners (not shown) to secure transducer 400 to a lower portion. Other methods of securing transducer 400 to a lower portion may be used, such as welding, bonding, etc.

Figure 32:
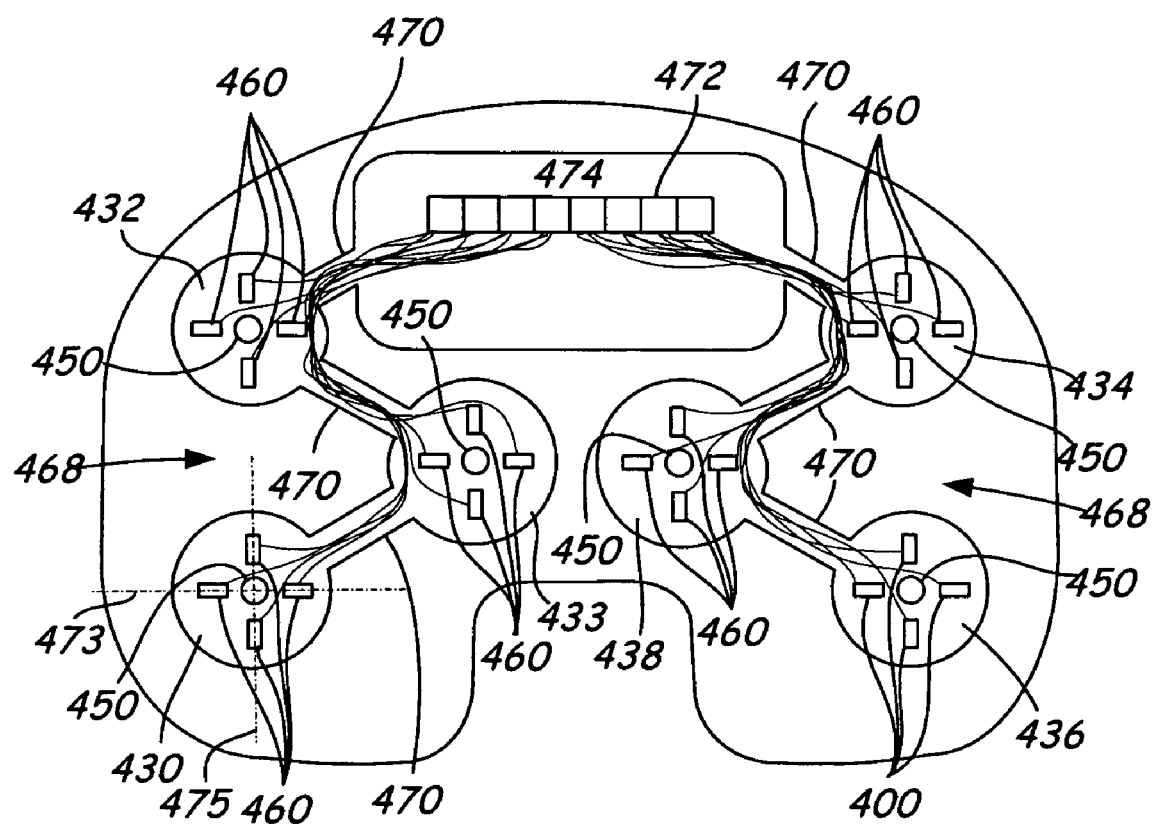
FIG. 32 is a bottom view of a transducer with electrical leads.

FIG. 32 illustrates a bottom plan view of transducer 400 wherein electrical leads from the sensors 460 are shown. Each of the medial plate 402 and the lateral plate 404 has an associated set of three support posts and three flexures arranged in an isosceles configuration. As illustrated, each set has a routing network 468 including channels 470 that provide pathways for electrical leads from strain gauges located in cavities 430, 432, 433, 434, 436, and 438. All electrical leads of the strain gauges are connected to a suitable connector or terminal strip 472 placed in cavity 474. Additional leads can connect terminal strip 472 to other circuitry that will acquire transducer data, process the data and transmit the data outside the body.

Sensors 460 are positioned in an "x" configuration, with eight gauges (four pairs) orthogonally arranged about a cylindrical post 450. Any number of sensing elements may be used. In the embodiment illustrated, the eight gauges in each flexure are connected in a conventional Wheatstone bridge configuration. The Wheatstone bridge configuration measures compressive loads on the flexures and minimizes cross talk from shear and torsion loads. As appreciated by those skilled in the art, suitable sensors may be used to measure shear and torsion loads acting on the medial tray 402 and lateral tray 404.

Each flexure has an associated channel 470 that ultimately routes electrical leads from sensors 460 to terminal strip 472. The channel 470 may be offset with respect to their respective sensors 460, for example at an angle of 45° between adjacent sensors. For example, with reference to cavity 430, the associated channel 470 is offset at an angle of 45° between the uppermost sensor and the rightmost sensor in cavity 430. Stated another way, the sensors 460 on each flexure are arranged in pairs with sensors from each pair positioned on opposite sides of the corresponding support post to define two orthogonal reference lines illustrated, for example, at 473 and 475. It has been discovered that by orienting channels 470 to be oblique to the aligned pairs of sensors, or oblique to reference lines 473 and 475 improves transducer performance. In one embodiment, all channels 470 are oblique to all pairs of sensors. Minimizing the number of channels 470 exiting a flexure and offsetting the channel with respect to associated sensors enhances accuracy and/or predictability of signals obtained by sensors 460. As a result, signals obtained include a more accurate representation of forces.

Figure 33:
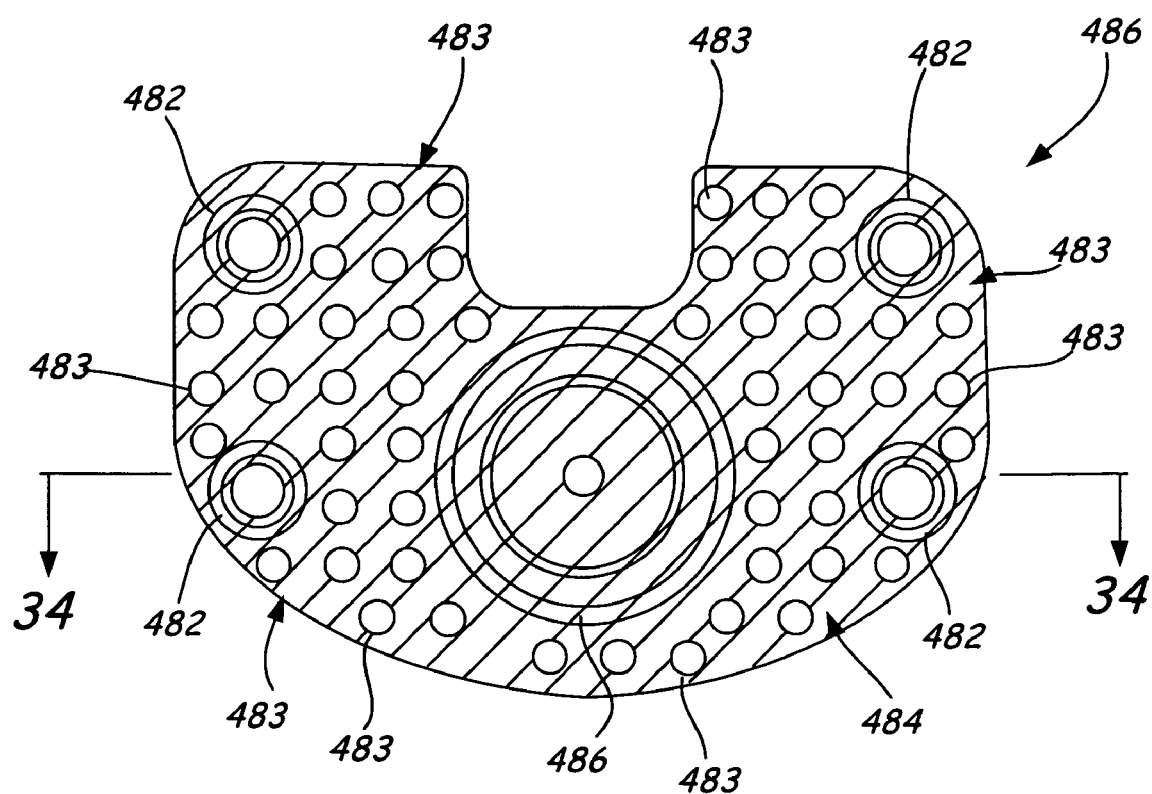
FIG. 33 is a top view of a lower portion.
Figure 34:
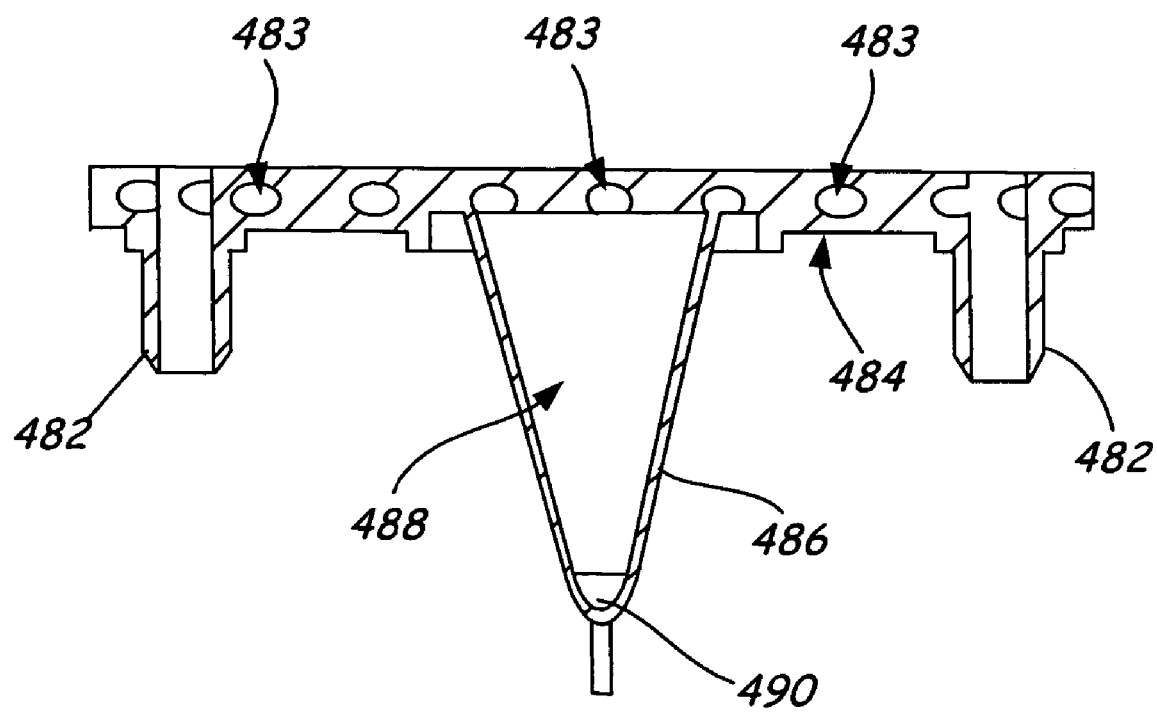
FIG. 34 is a cross sectional view of a lower portion.

FIGS. 33-34 illustrate a lower portion 480, which can be secured to transducer 400. Lower portion 480 includes spikes 482 that secure the transducer 400 to tibia 4 (FIG. 1). The spikes 482 are hollow to allow bone growth from tibia 4 through lower portion 480, which provides increased stability and damping of forces throughout the knee joint. Additionally, a plurality of apertures 483 on major surface 484 and around the circumference of lower portion 480 are connected to passageways and also allows soft tissue growth from tibia 4 through lower portion 480. The apertures 482 are connected to passageways for tissue growth; however, it should be understood the location of apertures 482 and orientation of passageways connected therebetween can vary as desired. Cone shaped portion 486 of lower portion 480 includes a pocket 488 for storage of circuitry 490. Pocket 488 opens toward transducer 400. Circuitry 490 is coupled to terminal strip 472 and is used to acquire, process and transmit transducer data.

Figure 35:
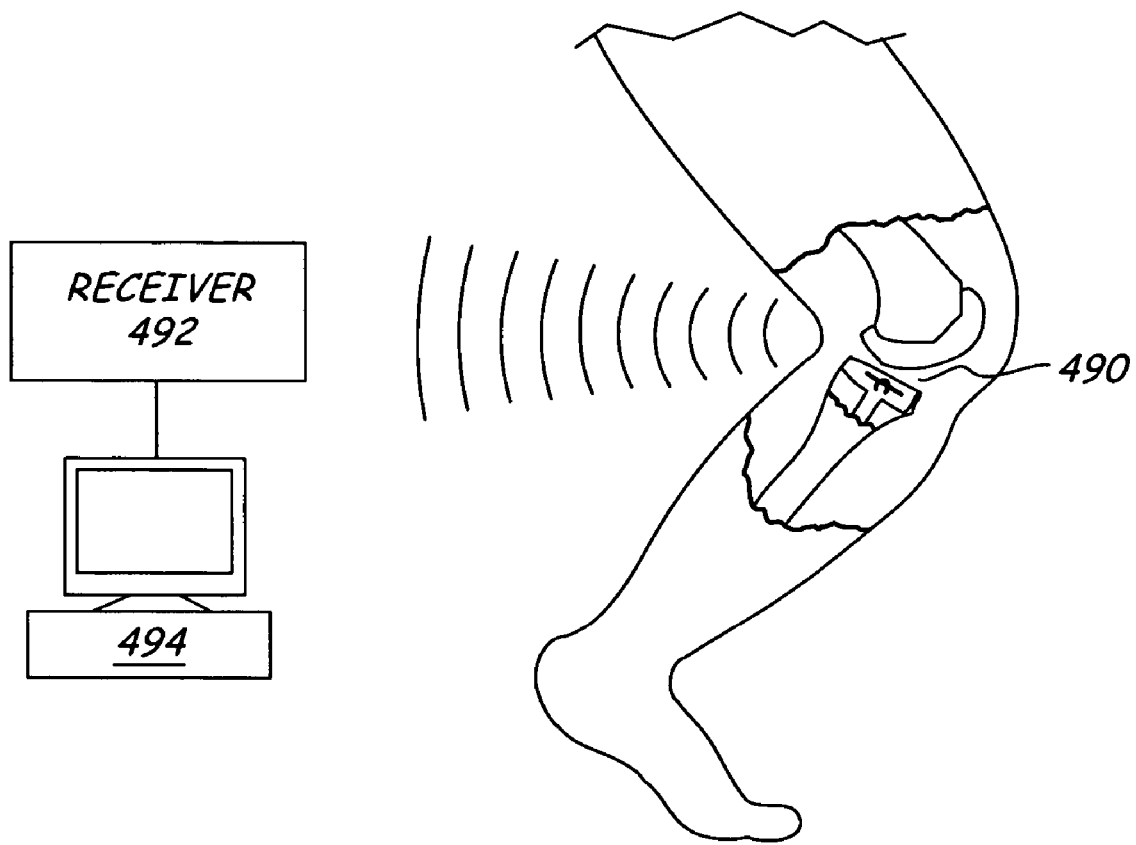
FIG. 35 is a schematic diagram of a telemetry system.

As illustrated in FIG. 35, circuitry 490 can be a telemetry device that transmits signals wirelessly to a receiver 492. Location of circuitry 490 in pocket 488 of portion 480 provides an area for storage that is secure. More importantly though, the location below the transducer 400 and thus on the tibia does not interfere with operation or stability of the knee joint. Receiver 492 can then transmit signals received from a telemetry device incorporating circuitry 490 to a computer 494 for further analysis.

As discussed above, the assembly accurately measures forces present on the prosthesis in vivo or in vitro as the knee joint is articulated through partial or complete range of movements. The resulting data is collected and transmitted wirelessly for analysis to ensure proper force load distribution across the load bearing surfaces of the knee joint prosthesis. With proper load distribution, the knee joint prosthesis is optimally aligned thereby realizing increased prosthetic life.

Measurements obtained provide valuable information for research, surgery and rehabilitation. For surgical applications, transducer 400 may provide data that aids in identifying locations where bone needs to be added or removed to properly align the components of the prosthesis. Periodic monitoring of the assembly using telemetry allows for systematic and timely diagnosis of potential problems within the assembly.

Although the present invention has been described with reference to preferred embodiments, workers skilled in the art will recognize that changes may be made in form and detail without departing from the spirit and scope of the invention.

What is claimed is:

1. A prosthesis comprising:
   a unitary body, comprising:
      a first plate;
      a second plate spaced apart from a side of the first plate to form a gap therebetween such that forces placed upon the second plate are isolated from the first plate;
      a lower plate having a first flexure and a second flexure positioned therein, the lower plate being spaced apart from a bottom of the first plate and a bottom of the second plate;
      a first support post aligned with the first flexure and connecting the bottom of the first plate with a top of the lower plate such that forces placed upon the first plate are transmitted to the first flexure;
      a second support post aligned with the second flexure and connecting the bottom of the second plate with the top of the lower plate such that forces placed upon the second plate are transmitted to the second flexure; and
      a plurality of force sensors provided in the first and second flexures to sense strain therein.

2. The prosthesis of claim 1 and further comprising third and fourth support posts connecting the bottom of the first plate with the top of the lower plate and fifth and sixth support posts connecting the bottom of the second plate with the top of the lower plate.

3. The prosthesis of claim 2 wherein the first, third and fourth support posts are arranged in an isosceles triangle configuration and wherein the second, fifth and sixth support posts are arranged in an isosceles triangle configuration.

4. The prosthesis of claim 3 wherein the lower plate further comprises three flexure members aligned with the first, third and fourth support posts and three flexure members aligned with the second, fifth and sixth support posts.

5. The prosthesis of claim 1 and further comprising a first insert carried by the first plate and a second insert carded by the second plate.

6. The prosthesis of claim 5 and further comprising a condylar component adapted to engage the first insert and the second insert to form an articulation joint.

7. The prosthesis of claim 1 and further comprising a cover plate attached to the lower plate, the cover plate having a major surface and a plurality of apertures disposed substantially throughout the major surface to accommodate growth of tissue, vessels and nerves.

8. The prosthesis of claim 1 wherein the first and second support posts are round.

9. The prosthesis of claim 1 wherein the first and second support posts include fillets.

10. The prosthesis of claim 4 wherein the three flexure members aligned with the first, third and fourth posts include force sensors to sense strain therein and wherein the three flexure members aligned with the second, fifth and sixth posts include force sensors to sense strain therein.

11. A knee joint prosthesis adapted to be positioned between a tibia and a femur, comprising:
   a femoral component adapted to be secured to the femur and including a medial condylar surface and a lateral condylar surface;
   a tibial component adapted to be secured to the tibia and comprising:
      a medial insert adapted to engage the medial condylar surface;
      a lateral insert adapted to engage the lateral condylar surface; and a unitary body, comprising:
- a medial plate adapted to carry the medial insert;
- a lateral plate adapted to carry the lateral insert and spaced apart from the medial plate to isolate forces placed upon the lateral plate from the medial plate;
- a lower plate having a first plurality of flexures and a second plurality of flexures, the lower plate adapted to be positioned closer to the tibia than the medial plate and the lateral plate and spaced apart from the medial plate and the lateral plate;
- a first plurality of support posts connecting the medial plate with the lower plate such that forces placed upon the medial plate are transmitted to the first plurality of flexures; and
- a second plurality of support posts connecting the lateral plate with the lower plate such that forces placed upon the lateral plate are transmitted to the second plurality of flexures.

12. The prosthesis of claim 11 wherein the first plurality of spaced apart flexures are aligned with the first plurality of support posts and the second plurality of spaced apart flexures are aligned with the second plurality of support posts.

13. The prosthesis of claim 12 wherein the first plurality of support posts includes three support posts and the second plurality of support posts includes three support posts.

14. The prosthesis of claim 13 wherein the first plurality of support posts are arranged in a isosceles triangle configuration and wherein the second plurality of support posts are arranged in a isosceles triangle configuration.

15. The prosthesis of claim 14 wherein the medial plate includes three spaced apart flexures aligned with the first plurality of support posts and the lateral plate includes three spaced apart flexures aligned with the second plurality of support posts.

16. The prosthesis of claim 11 wherein the first and second plurality of support posts are round.

17. The prosthesis of claim 1 wherein the force sensors are strain gauges.

18. The prosthesis of claim 1 wherein the plurality of force sensors independently measure forces reacted by the first flexure and independently measure forces reacted by the second flexure.

19. The prosthesis of claim 1 wherein the first plate deflects under compressive loads.

20. The prosthesis of claim 19 wherein the second plate deflects under compressive loads.

21. The prosthesis of claim 1 and further comprising a cover plate attached to the lower plate.

22. The prosthesis of claim 11 and further comprising a first plurality of force sensors provided in the first plurality of flexures to sense strain therein and a second plurality of force sensors provided in the second plurality of flexures to sense strain therein.

23. The prosthesis of claim 22 wherein the force sensors are strain gauges.

24. The prosthesis of claim 22 wherein the first plurality of force sensors independently measure forces reacted by the first plurality of flexures and wherein the second plurality of force sensors independently measure forces reacted by the second flexure.

25. The prosthesis of claim 11 wherein the medial plate and lateral plate deflect under compressive loads.

26. The prosthesis of claim 11 and further comprising a cover plate attached to the lower plate.

* * * * *